United States Patent [19]
Meyer

[11] Patent Number: 5,633,284
[45] Date of Patent: May 27, 1997

[54] NITROUS OXIDE CONTAINING DERMATOLOGICAL COMPOSITION

[75] Inventor: Petrus J. Meyer, Randburg, South Africa

[73] Assignee: Pitmy International N.V., Netherlands

[21] Appl. No.: 318,626

[22] PCT Filed: Jun. 3, 1993

[86] PCT No.: PCT/EP93/01405

§ 371 Date: Feb. 13, 1995

§ 102(e) Date: Feb. 13, 1995

[87] PCT Pub. No.: WO93/25213

PCT Pub. Date: Dec. 23, 1993

[30] Foreign Application Priority Data

Jun. 8, 1992 [ZA] South Africa ............ 92/4153

[51] Int. Cl.$^6$ ............ A61K 31/075; A61K 31/20
[52] U.S. Cl. ............ 514/718; 514/560; 514/825; 514/859; 514/861; 514/863; 514/880
[58] Field of Search ............ 424/60, 718; 514/825, 514/859, 861, 863, 560, 880

[56] References Cited

FOREIGN PATENT DOCUMENTS

| 0213827 | 3/1987 | European Pat. Off. . |
| 1033299 | 7/1963 | United Kingdom . |
| 1105919 | 9/1965 | United Kingdom . |

*Primary Examiner*—Shelley A. Dodson
*Attorney, Agent, or Firm*—Nikaido, Marmelsteing, Murray & Oram, LLP

[57] ABSTRACT

Dermatological compositions comprising nitrous oxide and at least one essential fatty acid or lower alkyl ester thereof in a dermatologically acceptable carrier medium is useful in the treatment of a variety of skin, muscle and joint disorders including psoriasis, shingles, fever blisters, chicken pox, ache, chilblains, eczema, chloasmas, alopecia, dermatitis, ringworm and burn wounds. The composition preferably also includes additional ingredients selected from coal tar, collagen, nicotinamide, nicotinic acid, lanolin, vitamin E, methyl salicylate, arnica, and $H_1$-antagonist antihistamines or combinations thereof.

13 Claims, No Drawings

NITROUS OXIDE CONTAINING DERMATOLOGICAL COMPOSITION

FIELD OF THE INVENTION

This invention relates to dermatological compositions. The compositions of this invention are suitable to be applied to the human skin for the treatment of a variety of skin, muscular, joint and peripheral circulatory conditions.

BACKGROUND OF THE INVENTION

It is known in the field of dermatology to make use of coal tar preparations in the treatment of certain skin conditions, for example, psoriasis [Hunter J. A. A., Savin J. A. and Dahl M. V., *Clinical Dermatology*, Blackwell Scientific Publications p.49].

It has also been suggested that essential fatty acids, including evening primrose oil may be used in the treatment of skin conditions such as eczema [see references cited by July Graham, *Evening Primrose Oil*, Thorsons, pp. 127–128].

Various other compositions are known to be used in the treatment of these and other skin conditions.

OBJECT OF THE INVENTION

It is an object of the present invention to provide novel dermatological compositions.

SUMMARY OF THE INVENTION

According to the present invention there is provided a dermatological composition having as active ingredients nitrous oxide and at least one essential fatty acid or ester thereof selected from the group consisting of linoleic acid, arachidonic acid, linolenic acid, gamma-linolenic acid, and the lower alkyl esters thereof in a dermatologically acceptable carrier.

The composition may further include one or more supplementary ingredients selected from the group consisting of Liquor Picis Carbonis [also known as coal tar solution], collagen, nicotinamide, nicotinic acid, lanolin, vitamin E, methyl salicylate, and known $H_1$-antagonist antihistamines.

In the preferred form of the invention the composition is saturated with nitrous oxide.

Also in the preferred form of the invention the essential fatty acid component of the composition comprises a mixture of esters of the fatty acids listed above. Thus in the most preferred form of the invention the fatty acid component of the composition is constituted by the complex known as Vitamin F and in this regard it is preferred to make use of the ester form of Vitamin F known as Vitamin F Ethyl Ester. This product is commercially available under the trade description of Vitamin F Ethyl Ester CLR 110 000 Sh.L. U./g from CLR Chemicals Laboratorium Dr. Kurt Richter GmbH, of Berlin, Germany. The typical fatty acid distribution of this product is as follows:

| | | |
|---|---|---|
| $<C_{16}$ | | 0% |
| $C_{16-0}$ | | 8,3% |
| $C_{18-0}$ | | 3,5% |
| $C_{18-1}$ | | 21,7% |
| $C_{18-2}$ | | 34,8% |
| $C_{18-3}$ | | 28,0% |
| $>C_{18}$ | | 1,6% |
| unknown | | 2,1% |

In one preferred form of the invention the composition comprises only coal tar solution as a supplementary active ingredient. In this form of the invention the composition is useful in the treatment of psoriasis, fever blisters, herpes simplex, shingles, chicken pox and eczematous conditions of the skin and scalp.

In another form of the invention the composition comprises coal tar solution in combination with one of collagen, nicotinamide, and lanolin. In these forms of the invention the composition has been shown to be useful for the treatment of ache, conditions involving poor peripheral circulation, such as chilblains, and uhthyoses respectively.

In an alternative form of the invention the composition may contain coal tar solution in combination with an antihistamine selected from the $H_1$-antagonist group and be used for the treatment of atopic and allergic conditions manifesting in skin irritations, such as eczema, dermatitis and ringworm.

In a further form of the invention the supplementary ingredient may comprise methyl salicylate in which form the composition is useful in the treatment of muscle and joint pains.

The composition may finally comprise collagen and lanolin as supplementary ingredients in which form it is useful in cosmetic preparations, or for the treatment of alopecia or minor skin ailments, such as chloasmas.

The composition may be formulated to have any dermatologically acceptable consistency, i.e. as a lotion, cream, ointment or gel.

EXAMPLES OF THE INVENTION

Without thereby limiting the scope of the invention some examples will now be described to illustrate the invention.

EXAMPLE 1

Dermatological composition useful in treatment of psoriasis

Five liters of water was saturated with $N_2O$ at room temperature in a pressure vessel. 75 g of vitamin F ethyl ester, 50 g vitamin E and 50 g chremaphor was mixed and heated to about 80° C. and the mixture was emulsified in the $N_2O$ saturated water with stirring. 500 ml of a prepared coal tar solution BP73 [also known as Liquor Picis Carbonis] was produced by dissolving 100 g of prepared coal tar BP73 in 375 g of ethyl alcohol with the addition of Polysorbate 80. The coal tar solution was saturated with $N_2O$ in a pressure vessel and mixed with the above emulsion. The viscosity of the solution was modified according to technique known in the trade i.e. with xanthan gum to provide a gel. In this regard it is preferred to use Keltrol ® TF, a product marketed commercially by the Kelco Division of Merck & Co., Inc. If desired a suitable preservative such as a parabenz compound may be added.

The resulting gel was used in the treatment of 53 psoriasis sufferers. All these sufferers had previously attempted alternative forms of psoriasis medication and treatment and without success. Such treatments included UV radiation, coal tar, cortizone and etretinate preparations and even Dead Sea baths. The patients applied the gel as described above to the affected areas 2 or 3 times daily. Of those treated 88.7% reported a definite improvement in their condition. On average the period of treatment before positive results were seen was 3 weeks. In 6% of the cases it took more than 6 weeks of treatment before improvements were seen. 72% of the patients treated were considered to have derived long term results from the use of the gel described above as evidenced by the clearing and sustained absence of lesions for a period of more than 3 months. Such long term results were achieved on average after 8.5 weeks of treatment. In treating patients with a gel it is preferred to use a suitable skin moisturiser with the gel to prevent drying out of the skin. Such moisturising ingredients may of course also be incorporated into the composition of the invention to produce a cream formulation which may then be used as a supplementary treatment with the gel formulation.

EXAMPLE 2

Alternative dermatological composition for use in treatment of psoriasis and fever blisters [Herpes Simplex infection] and eczematous skin conditions An alternative dermatological composition was made up to contain the following ingredients in the quantities stated per 100 g of final product:

|  | gram |
| --- | --- |
| Prepared coal tar BP1973 | 1,00 |
| Vitamine F Ethyl Ester | 1,50 |
| Nitrous Oxide [$N_2O$] | qs |
| Polysorbate 80 [emulsifier] | 0,25 |
| Ethyl Alcohol [solvent/dispersant] | 3,75 |
| PEG-40 [Hydrogenated caster oil - as solubilizer] | 0,45 |
| Vitamine E [dl-alpha Tocopherol - as antioxidant] | 0,30 |
| Sodium propyl paraben [as preservative] | 0,05 |
| Methyl paraben [as preservative] | 0,10 |
| Xanthan Gum | 0,8-0.9 |
| Water | balance |
|  | 100 |

The coal tar and polysorbate 80 [Criliet 4] were mixed with warming to render it fluid and poured into about 75% of the ethyl alcohol with stirring which was continued for 1 hour to achieve dispersion. The mixture was allowed to cool for 24 hours, the supernatant was decanted through a filter and the mixing vessel and filter were washed with part of the remaining alcohol added thereto. The resulting solution was charged with $N_2O$ gas by maintaining the solution in a pressure vessel under $N_2O$ at 2 bar for 96 hours. The $N_2O$ charged coal tar solution was stored in a cool place.

The water fraction of the composition was prepared by charging the water with $N_2O$ for 48 hours at 2 bar as described above. Again, the $N_2O$ charged water was kept in a cool place.

A Third sub-mixture was prepared by mixing together and heating to 80° C. the Vitamin F, Vitamin E and PEG-40 hydrogenated castor oil. Once mixed the methyl paraben was added with stirring to obtain a homogenous mixture of oil miscible fractions. This mixture was kept at 80° C. and added with stirring into part of the $N_2O$ charged water which had previously been prepared and provided with the sodium propyl paraben to produce an oil-in-water emulsion.

Finally, the balance of the $N_2O$ charged water, the charged coal tar solution and the oil-in-water emulsion were mixed with stirring while granulated xanthan gum was slowly added to the mixture in sufficient quantity to achieve a viscosity of 1740 cps.

The gel is passed through a 60 mesh sieve and packaged into scalable containers.

The gel formulated as set out adore is presently undergoing double blind crossover clinical trials against aqueous cream as placebo for the treatment of fever blisters [Herpes Simplex infection]. It is expected that the results will confirm earlier results obtained in uncontrolled trials in which the composition was found effective against such infections as well as to provide relief to patients suffering from shingles, chicken pox, psoriasis and eczematous conditions of the skin.

EXAMPLE 3

Dermatological composition for use in the treatment of eczema and dermatitis

A composition having the components as set out in Example 2 but with the addition of 1 g diphenhydramine hydrochloride and made up as therein described was found in uncontrolled trials to bring relief and remission to patients suffering from atopic eczema as well as to patients suffering from dermatits.

EXAMPLE 4

Composition for treatment of chilblains

A composition as described in Example 2 to which 1 g of nicotinic acid had been added was reported by patients to relieve the symptoms of chilblains and to restore healthy skin.

EXAMPLE 5

Composition for treatment of acne and scar tissue

A composition as described in Example 2 was made up with the further addition of 1.5 g collagen and 1.5 g lanolin.

This composition was successfully tested on persons suffering from ache vulgaris and was found not only to clear up the condition but also to result in visual improvement of appearance of the formerly heavily blemished skin.

The same composition was also used by a 13 year old patient some one year after she had suffered extensive third degree burn wounds on the face, shoulders and back. Encouraging signs of repair of the scarred skin was observed.

EXAMPLE 6

Composition for treatment of fibrositis, muscle cramps, and improvement of peripheral circulation A composition as described in Example 2 but not including coal tar, polysorbate 80 and alcohol was made up substantially as therein described. This composition was found in several trials to give substantial relief of fibrositis and muscular cramps when topically applied. It was also reported by patients to relieve swelling following tissue trauma such as caused by bumps or falls giving rise to impaired blood circulation. Some patients found that the effect of this composition was enhanced after the addition thereto of methyl silicate or arnica.

EXAMPLE 7

Cosmetic Composition

A composition as described in Example 2 but omitting the coal tar, polysorbate 80 and alcohol and with the addition of 1.5 g collagen. 1.5 g lanolin and 1.5 g additional Vitamin E resulted in a cosmetic product which was found to be suitable for the removal of chloasmas, warts and moles and which also stimulated hair growth in alopecia cases.

Many variations of the invention may be devised without departing from the scope and spirit of the invention.

I claim:

1. A topical composition, comprising as active ingredients, nitrous oxide and at least one essential fatty acid or lower alkyl ester thereof, selected from the group consisting of linoleic acid, arachidonic acid, linolenic acid and gamma-linolenic acid, in combination with a dermatologically acceptable carrier.

2. A topical composition according to claim 1, further comprising at least one supplementary active ingredient selected from the group consisting of coal tar solution, collagen, nicotinamide, nicotinic acid, lanolin, vitamin E, methyl salicylate, and an $H_1$-antagonist antihistamine.

3. A topical composition according to claim 2, wherein the composition is saturated with nitrous oxide.

4. A topical composition according to claim 1, wherein the at least one essential fatty acid or lower alkyl ester thereof comprises a mixture of esters of the fatty acids set out therein.

5. A composition according to claim 1, wherein the at least one essential fatty acid or lower alkyl ester thereof is Vitamin F Ethyl Ester.

6. A composition according to claim 2, wherein the at least one supplementary active ingredient is coal tar solution.

7. A composition according to claim 2, wherein the at least one supplementary active ingredient is coal tar solution and a second supplementary active ingredient selected from the group consisting of collagen, nicotinamide and lanolin.

8. A composition according to claim 2, wherein the at least one supplementary active ingredient is coal tar solution and an $H_1$-antagonist antihistamine.

9. A composition according to claim 2, wherein the at least one supplementary active ingredient is methyl salicylate.

10. A composition according to claim 2, wherein the at least one supplementary active ingredient is collagen and lanolin.

11. A method of treating a condition selected from the group consisting of skin, muscular, joint and peripheral circulatory condition in a patient in need of such treatment, comprising applying topically to the skin of the patient a condition-treating effective amount of a topical composition according to claim 1.

12. A composition according to claim 1, further comprising coal tar solution as a supplementary active ingredient.

13. A composition according to claim 1, wherein the at least one essential fatty acid or lower alkyl ester thereof is Vitamin F Ethyl Ester, and the composition further comprises coal tar solution as a supplementary active ingredient.

* * * * *